(12) United States Patent
Ueno et al.

(10) Patent No.: US 11,253,550 B2
(45) Date of Patent: Feb. 22, 2022

(54) METHOD FOR TREATING FIBROTIC LIVER DISEASE

(71) Applicant: ROHTO PHARMACEUTICAL CO., LTD., Osaka (JP)

(72) Inventors: Yui Ueno, Osaka (JP); Hidenori Nonaka, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 196 days.

(21) Appl. No.: 16/490,777

(22) PCT Filed: Feb. 22, 2018

(86) PCT No.: PCT/JP2018/006363
§ 371 (c)(1),
(2) Date: Sep. 3, 2019

(87) PCT Pub. No.: WO2018/159431
PCT Pub. Date: Sep. 7, 2018

(65) Prior Publication Data
US 2020/0009195 A1 Jan. 9, 2020

(30) Foreign Application Priority Data
Mar. 3, 2017 (JP) .............................. JP2017-040341

(51) Int. Cl.
*A61K 35/28* (2015.01)
*A61P 1/16* (2006.01)

(52) U.S. Cl.
CPC ................ *A61K 35/28* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 9,775,890 B2 * | 10/2017 | Stephenne | A61K 38/58 |
| 10,238,692 B2 | 3/2019 | Yang et al. | |
| 2010/0323027 A1 * | 12/2010 | Lim | A61K 35/28 |
| | | | 424/520 |
| 2013/0302291 A1 | 11/2013 | Stephenne et al. | |
| 2015/0037291 A1 | 2/2015 | Stephenne et al. | |
| 2016/0187317 A1 | 6/2016 | Sugi et al. | |
| 2017/0042940 A1 | 2/2017 | Stephenne et al. | |
| 2017/0354723 A1 * | 12/2017 | Stephenne | A61K 38/55 |
| 2018/0066231 A1 | 3/2018 | Ikeyama et al. | |
| 2018/0344775 A1 * | 12/2018 | Kurata | A61P 1/16 |
| 2018/0371417 A1 | 12/2018 | Yamahara et al. | |
| 2019/0062710 A1 * | 2/2019 | Betancourt | A61K 35/12 |
| 2019/0086389 A1 | 3/2019 | Sugii et al. | |
| 2020/0016211 A1 * | 1/2020 | Ueno | A61K 35/28 |
| 2020/0319161 A1 | 10/2020 | Sugii et al. | |

FOREIGN PATENT DOCUMENTS

| | | | |
|---|---|---|---|
| JP | 2004290189 A | | 10/2004 |
| JP | 2012508733 A | | 4/2012 |
| JP | 2012157263 A | | 8/2012 |
| JP | 2015508054 A | | 3/2015 |
| JP | 2016/140346 A | * | 8/2016 |
| JP | 2016/144439 A | * | 8/2016 |
| JP | 2016140346 A | | 8/2016 |
| JP | 2016144439 A | | 8/2016 |
| WO | 2012101181 A1 | | 8/2012 |
| WO | 2015016785 A1 | | 2/2015 |
| WO | 2016136986 A1 | | 9/2016 |
| WO | 2017010417 A1 | | 1/2017 |
| WO | 2017086356 A1 | | 5/2017 |
| WO | 2018125968 A1 | | 7/2018 |

OTHER PUBLICATIONS

Y.W. Eom et al.; "Mesenchymal stem cell therapy for liver fibrosis", The Korean Journal of Internal Medicine, vol. 30, No. 5, Sep. 2015, pp. 580-589 (10 pages).
M. Patrikoski et al.; "Development of fully defined xeno-free culture system for the preparation and propagation of cell therapy-compliant human adipose stem cells", Stem Cell Research & Therapy, 2013, pp. 1-15 (15 pages).
J.J. Bara et al.; "Concise Review: Bone Marrow-Derived Mesenchymal Stem Cells Change Phenotype Following in Vitro Culture: Implications for Basic Research and the Clinic", Stem Cells, 2014, pp. 1713-1723 (11 pages).
Extended European Search Report issued in corresponding European Application No. 18760778.3, dated Oct. 12, 2020 (10 pages).
Extended European Search Report issued in corresponding European Application No. 18760998.7, dated Oct. 26, 2020 (9 pages).
A. Watanabe, Handbook of Pathological Condition of Liver cirrhosis and Treatment, Medical Review, p. 12, Apr. 20, 2007 (2 pages) with Partial English Translation.
"Guideline for Liver Cirrhosis Medical Examination," edited by the Japanese Society of Gastroenterology, Nankodo Co., Ltd., p. 2, Oct. 2015 (3 pages) with Partial English Translation.
K. Kiyosawa et al., "Interrelationship of Blood Transfusion, Non-A, Non-B Hepatitis and Hepatocellular Carcinoma: Analysis by Detection of Antibody to Hepatitis C Virus," pp. 671-675, vol. 12, No. 4, Hepatology, Apr. 19, 1990 (5 pages).
M.F. Pittenger et al., "Multilineage Potential of Adult Human Mesenchymal Stem Cells," pp. 143-147, vol. 284, Science, Apr. 2, 1999 (6 pages).
A. Horinouchi et al., "Anticoagulant effects caused by low-serum culture with respect to adipose-derived mesenchymal stem cell," Extra edition of regenerative medicine—Journal of the Japanese Society for Regenerative Medicine, vol. 16, p. 300, O-26-2, Feb. 2017 (2 pages).

(Continued)

*Primary Examiner* — Ralph J Gitomer
(74) *Attorney, Agent, or Firm* — Osha Bergman Watanabe & Burton LLP

(57) ABSTRACT

The purpose of the present invention is to provide a novel therapeutic agent for liver disease. The present invention is a mesenchymal stem cell characterized by high expression of the Tissue Factor Pathway Inhibitor (TFPI). It is preferable that the mesenchymal stem cell is allogeneic and is derived from a fatty tissue. Moreover, the present invention includes a therapeutic agent for liver disease containing the mesenchymal stem cell.

2 Claims, 4 Drawing Sheets
Specification includes a Sequence Listing.

(56) References Cited

OTHER PUBLICATIONS

H. Ji et al., "Pig BMSCs Transfected with Human TFPI Combat Species Incompatibility and Regulate the Human TF Pathway in Vitro and in a Rodent Model," pp. 233-249, vol. 36, Cell Physiol Biochem, May 4, 2015 (17 pages).

Y. Ueno, "Review on effect of medium which influences human adipose tissue-derived MSC effect with respect to activated hepatic stellate cell strain LX-2," p. 302, vol. 16, Extra edition of regenerative medicine—Journal of the Japanese Society for Regenerative Medicine, Feb. 1, 2017 (2 pages).

Y. Sakai et al., "Research on regeneration therapy for chronic liver disease caused by adipose tissue-derived interstitial cell," pp. 29-30, The public welfare labor science research expense subsidy (research project for the urgent countermeasure to overcome hepatitis or the like) report for sharing research/Comprehensive research report, 2011 (8 pages).

D. Furlani et al., "Is the intravascular administratioin of mesenchymal stem cells safe? Mesenchymal stem cells and intravital microscopy," pp. 370-376, Microvascular Research, No. 77, Feb. 26, 2009 (7 pages).

K. Tatsumi et al., "Tissue factor triggers procoagulation in transplanted mesenchymal stem cells leading to thromboembolism," pp. 203-209, Biochemical and Biophysical Research Communications, No. 431, Jan. 9, 2013 (7 pages).

S. Shiratsuki et al., "Enhanced survival of mice infused with bone marrow-derived as compared with adipose-derived mesenchymal stem cells," pp. 1353-1359, Hepatology Research, The Japan Society of Hepatology, Feb. 10, 2015 (7 pages).

S. H. Al-Saqi et al., "Defined serum-free media for in vitro expansion of adipose-derived mesenchymal stem cells," pp. 915-926, vol. 16, No. 7, Cytotherapy, Feb. 16, 2014 (12 pages).

International Search Report issued in corresponding International Application No. PCT/JP2018/006363; dated May 15, 2018 (2 pages).

Written Opinion of the International Searching Authority issued in corresponding International Application No. PCT/JP2018/006363; dated May 15, 2018 (5 pages).

International Search Report issued in corresponding International Application No. PCT/JP2018/006364; dated May 15, 2018 (1 page).

Written Opinion of the International Searching Authority issued in corresponding International Application No. PCT/JP2018/006364; dated May 15, 2018 (5 pages).

Office Action issued in corresponding Japanese Application No. 2019-502920, dated Nov. 24, 2021 (9 pages).

* cited by examiner

[Fig. 1]
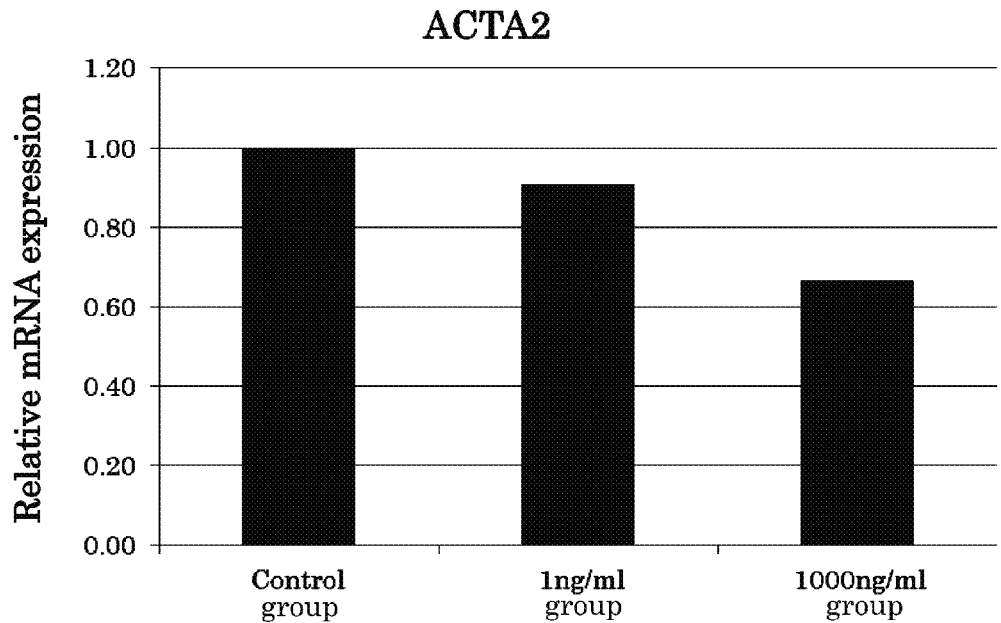
[Fig. 2]
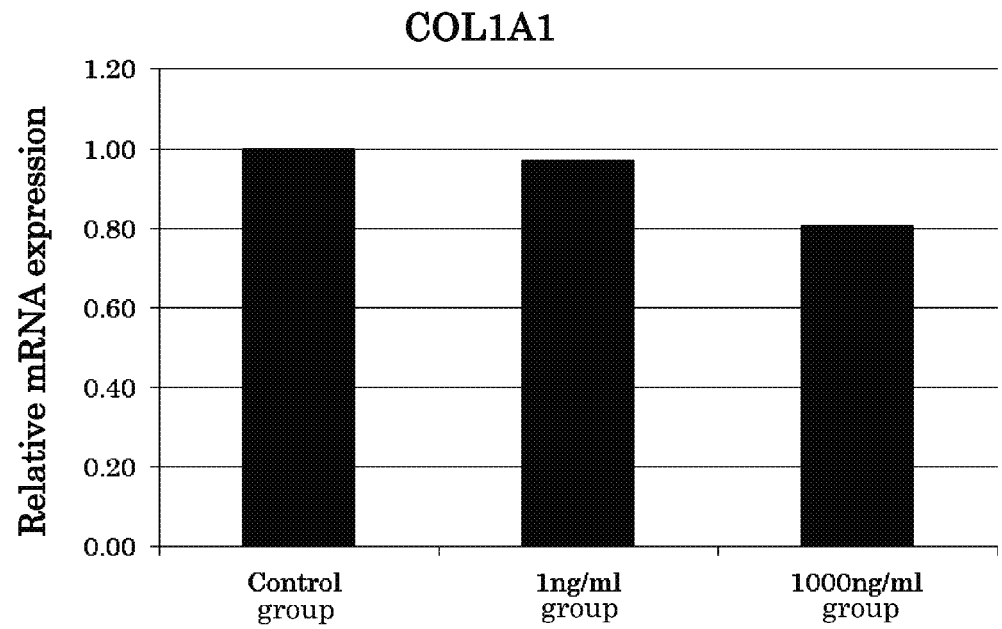

[Fig. 3]
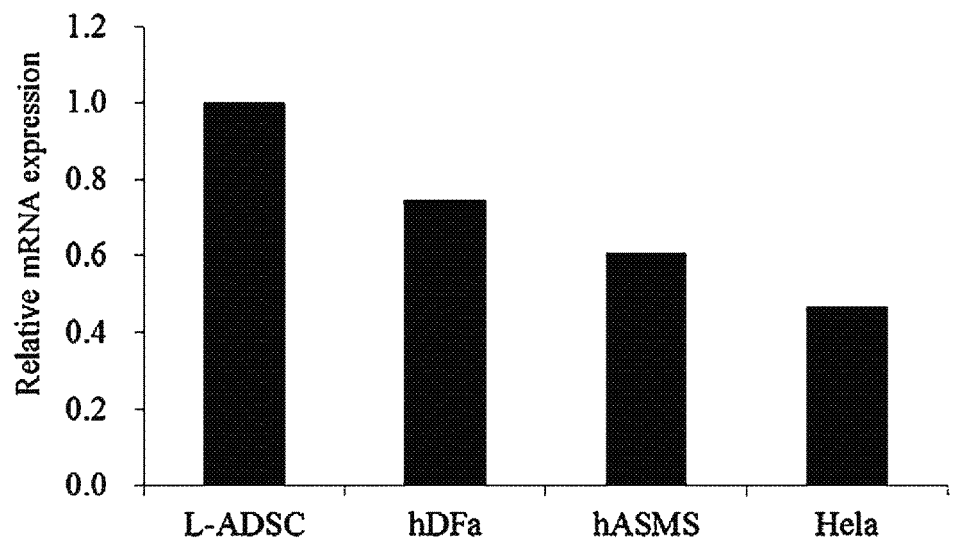
[Fig. 4]
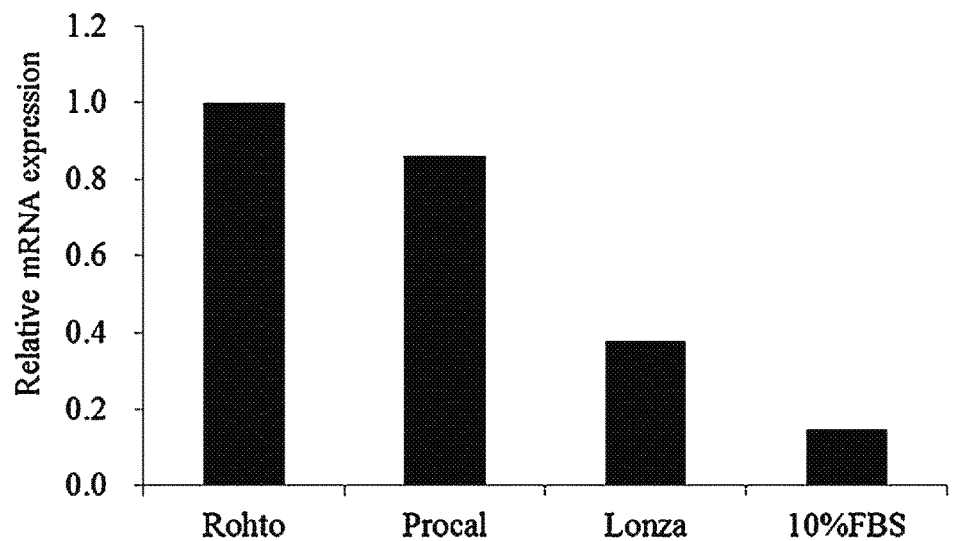
[Fig. 5]
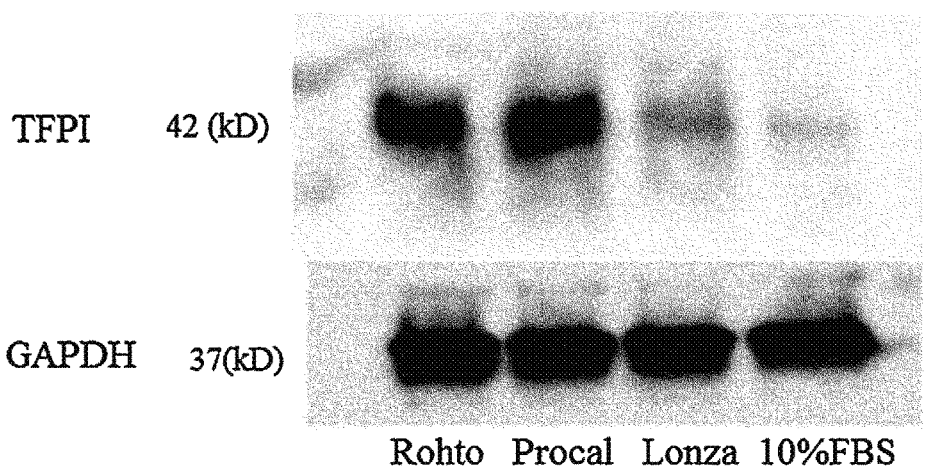

[Fig. 6]
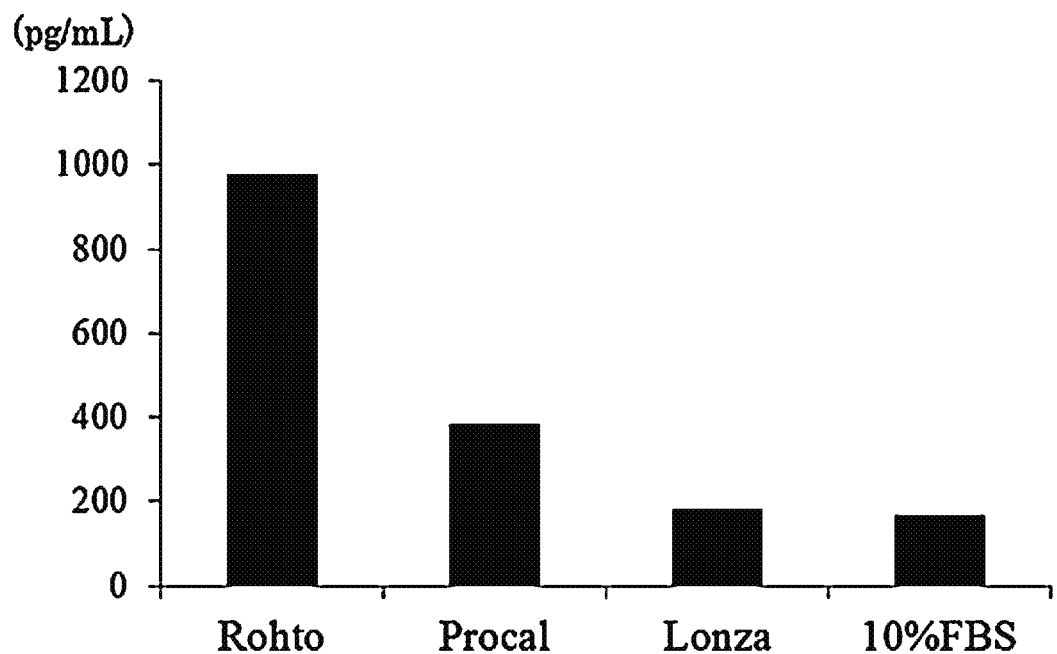
[Fig. 7]
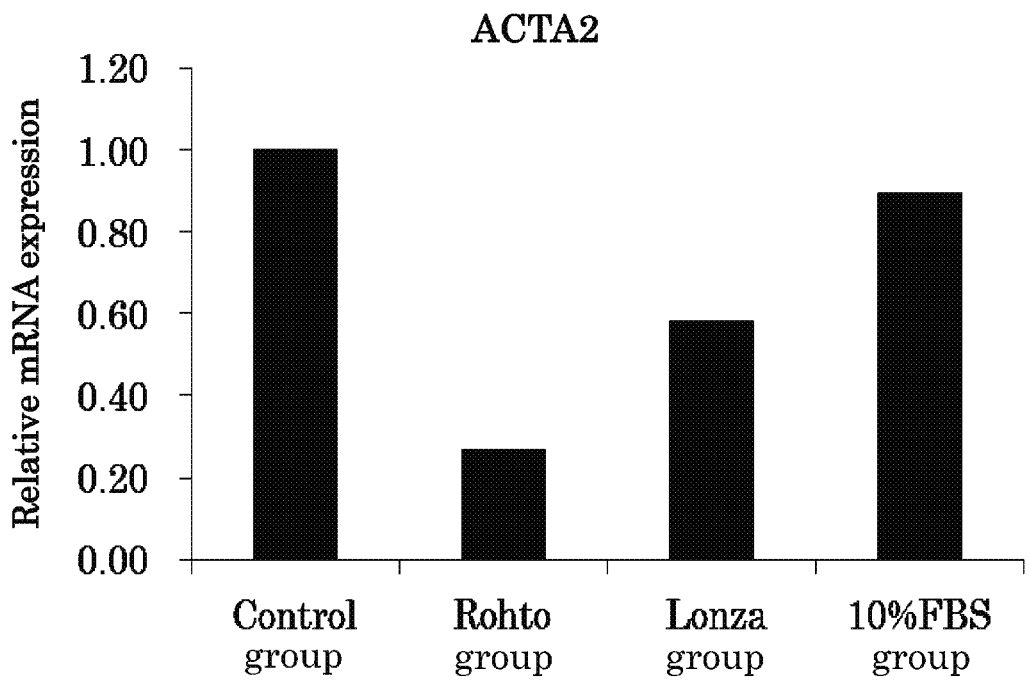

[Fig. 8]
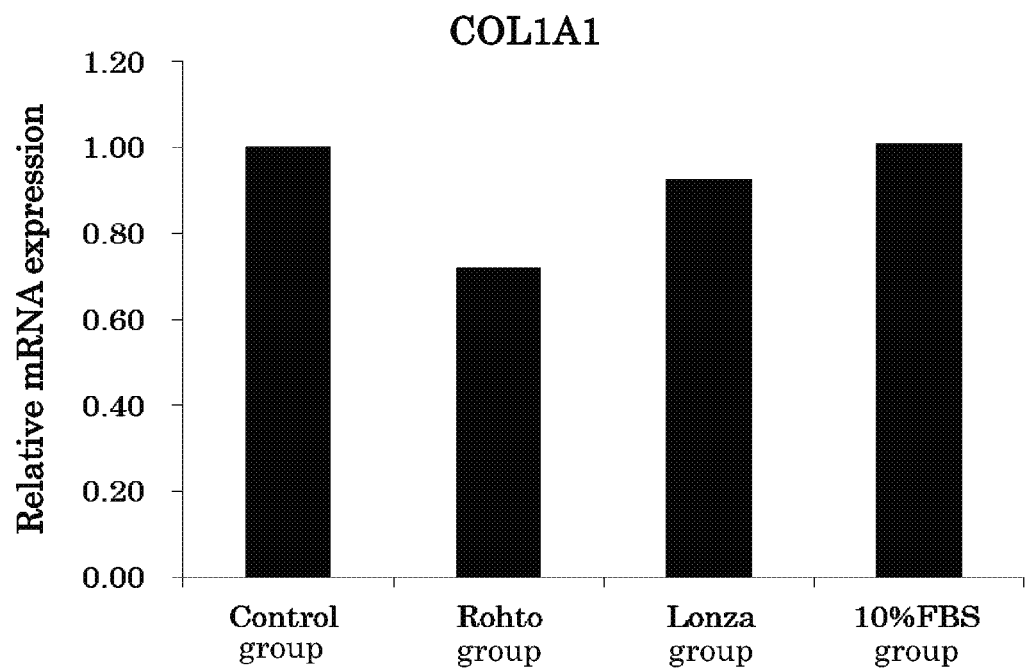

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
agatcgagaa catccggag                    19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agtactctcc actcttccag                   20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
ccttcatcgg gatggagtc                    19

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ccttcctgat gtcaatatca cac                23

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
ctgctgctta atcttgccc                    19

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
tggcaactcc gtatctgtg                    19

METHOD FOR TREATING FIBROTIC LIVER DISEASE

TECHNICAL FIELD

The present invention relates to mesenchymal stem cells and a therapeutic agent for liver disease.

Liver cirrhosis exhibiting remarkable fibrosis and formation of regenerative nodule is the terminal phase of various liver diseases and pathologically characterized by formation of false leaflets due to reconstruction of liver lobules and intrahepatic and extrahepatic hemodynamic abnormality resulting in hypofunction of liver cells (see Non Patent Document 1). Also in liver cirrhosis, it is known that a liver-cell degeneration/necrosis and regeneration process is repeated due to chronic inflammation, and extracellular matrix is excessively accumulated within the liver during the process, leading to fibrosis.

Examples of a cause of liver cirrhosis include persistent infection with a hepatitis virus, excessive alcohol intake, obesity, insulin resistance, autoimmunity (primary biliary cirrhosis, primary sclerosing cholangitis, autoimmune hepatitis), hereditary and medication (see, Non Patent Document 2). Of them, a hepatitis virus is a major cause, and particularly, hepatitis C virus (hereinafter referred to as "HCV") is the highest cause. The number of HCV careers is estimated as 170 million in the world and 1.5 to 2 million in Japan. About 70% of the HCV patients are persistently infected and developed into chronic hepatitis. Once developed into chronic hepatitis, the virus is rarely eliminated naturally; for example, the rate of elimination is 0.2% per year. Persistent inflammation caused by HCV infection induces liver fibrosis, which further develops into liver cirrhosis and hepatocellular carcinoma (see, Non Patent Document 3).

If liver cirrhosis develops from a compensation phase to a decompensation phase associated with further advanced fibrosis, the case cannot be sufficiently overcome by existing drugs and therapies. In the circumstance, it has been desired to develop a novel therapeutic agent different in action mechanism from the existing drugs.

Mesenchymal stem cells are precursor cells having pluripotency and isolated for the first time from the bone marrow by Friedenstein (1982) (Non Patent Document 4). It has been found that mesenchymal stem cells are present in various tissues including the bone marrow, umbilical cord and adipose, and transplantation of mesenchymal stem cells has been expected as a novel therapy for various intractable diseases (see, Patent Documents 1 and 2). Recently, it has been found that the stromal cells of an adipose tissue, placenta, umbilical cord, vitelline coat, etc. have the same function as that of the mesenchymal stem cells. Therefore, mesenchymal stem cells are sometimes referred to as mesenchymal stromal cells.

PRIOR ART DOCUMENTS

Patent Documents

Patent Document 1: JP 2012-157263 A
Patent Document 2: JP 2012-508733 A

Non Patent Documents

Non Patent Document 1: Akiharu Watanabe, Handbook of Pathological Condition of Liver cirrhosis and Treatment, Medical Review, published on Apr. 20, 2007, p.12

Non Patent Document 2: Guideline for Liver Cirrhosis Medical Examination, 2015, edited by the Japanese Society of Gastroenterology, Nankodo Co., Ltd., published in October 2015, P.2

Non Patent Document 3: Kiyosawa K. et. al., Hepatology, (1990), 12(4 Pt 1), pp.671-675

Non Patent Document 4: Pittenger F. M. et al., Science, (1999), 284, pp. 143-147

SUMMARY OF INVENTION

Technical Problem

In the circumstance, the present invention aims to provide a novel therapeutic agent for liver disease.

Solution to Problem

The present inventors conducted intensive studies with a view to attaining the aforementioned object. As a result, they found that mesenchymal stem (stromal) cells (MSC) expressing a Tissue Factor Pathway Inhibitor (TFPI) at a high level is effective for treating liver disease. Based on the finding, the present invention was accomplished. According to the present invention, it is possible to provide a therapeutic agent effective for treating liver disease. More specifically, the present invention is summarized as follows.

[1] Mesenchymal stem cells wherein the expression of Tissue Factor Pathway Inhibitor (TFPI) is high.

[2] The mesenchymal stem cells according to [1], wherein the mesenchymal stem cells are allogeneic.

[3] The mesenchymal stem cells according to [1] or [2], wherein the mesenchymal stem cells are derived from adipose tissue.

[4] A therapeutic agent for liver disease comprising the mesenchymal stem cells according to any one of [1] to [3].

[5] The therapeutic agent for liver disease according to [4], wherein the liver disease is liver disease associated with fibrosis of liver tissue.

[6] A method for treating liver disease characterized by using mesenchymal stem cells in which the expression of Tissue Factor Pathway Inhibitor (TFPI) is high.

[7] The method for treating liver disease according to [6], wherein the mesenchymal stem cells are allogenic.

[8] The method for treating liver disease according to [6] or [7], wherein the mesenchymal stem cells are derived from adipose tissue.

Advantageous Effects of Invention

According to the present invention, it is possible to provide a novel therapeutic agent for liver disease.

BRIEF DESCRIPTION OF DRAWINGS

FIG. 1 is a graph showing an effect of rTFPI for suppressing expression of a fibrosis related gene ACTA2 in hepatic stellate cells.

FIG. 2 is a graph showing an effect of rTFPI for suppressing expression of a fibrosis related gene COL1A1 in hepatic stellate cells.

FIG. 3 is a graph showing the comparison results of expression of TFPI mRNA in the mesenchymal stem cells of the present invention with those of other cells.

FIG. 4 a graph showing the comparison results of expression of TFPI mRNA in the mesenchymal stem cells of the present invention with other cells (mesenchymal stem cells under conventional culture conditions).

FIG. 5 is a photograph showing the comparison results of the expression level of TFPI protein in the mesenchymal stem cells of the present invention with that of other cells (mesenchymal stem cells obtained under conventional culture conditions).

FIG. 6 is a graph showing the comparison results of the secretion amount of TFPI protein in the mesenchymal stem cells of the present invention with that of other cells (mesenchymal stem cells obtained under conventional culture conditions).

FIG. 7 is a graph showing the comparison results of the effect of mesenchymal stem cells of the present invention for suppressing expression of a fibrosis related gene ACTA2 with that of other cells (mesenchymal stem cells obtained under conventional culture conditions).

FIG. 8 is a graph showing the comparison results of the effect of mesenchymal stem cells of the present invention for suppressing expression of a fibrosis related gene COLIA1 with that of other cells (mesenchymal stem cells obtained under conventional culture conditions).

DESCRIPTION OF EMBODIMENTS

The mesenchymal stem cells of the present invention and a therapeutic agent for liver disease will be described in detail.

[Mesenchymal Stem Cells]

The mesenchymal stem cells of the present invention are characterized in that expression of TFPI (Tissue Factor Pathway Inhibitor) is high.

TFPI is a glycoprotein having a molecular weight of about 42,000 and serving as a Kunitz protease inhibitor, which is considered to bind to a TF-activated VII factor via activated X factor and suppress blood coagulation activity of the factor [Broze, G. J., Proc. Natl. Acad. Sci., 84, p1886 (1987)]. TFPI is expressed mainly on vascular endothelial cells and bound onto the cell membrane. TFPI is known to be released when the bond is cleaved with thrombin, MMPs, heparin, etc.

The phrase "the expression of TFPI is high" include a case where the expression of TFPI mRNA is high; the expression of TFPI protein is high; or the both expressions are high.

The mesenchymal stem cells of the present invention are satisfactory if the expression of TFPI is high compared to other cells; more specifically, the mesenchymal stem cells of the present invention are satisfactory if the expression of TFPI is high compared to mesenchymal stem cells obtained under conventional culture conditions (for example, culture in a 10% FBS-containing DMEM medium), preferably 1.5 times or more, more preferably twice or more, further preferable 3 times or more and particularly preferably 5 times or more as high as that of mesenchymal stem cells obtained in conventional culture conditions.

The mesenchymal stem cells of the present invention are satisfactory if the expression of TFPI is high compared to skin fibroblasts, smooth muscle cells and epithelial cells; preferably 1.1 times or more, more preferably 1.15 times or more and further preferably 1.2 times or more as high as any one of skin fibroblasts, smooth muscle cells and epithelial cells. Particularly preferably, TFPI is expressed 1.1 times or more, further more preferably 1.15 times or more and more particularly preferably 1.2 times or more as high as two or more types of cells selected from skin fibroblasts, smooth muscle cells and epithelial cells. Further particularly preferably, TFPI is expressed 1.1 times or more, more preferably 1.15 times or more and most preferably 1.2 times or more as high as three or more types of cells of skin fibroblasts, smooth muscle cells and epithelial cells.

The term "mesenchymal stem cells" in the present invention refers to cells being capable of differentiating into one or more cells, preferably two or more cells, and further preferably three or more cells belonging to the mesenchyme (bone cells, cardiomyocytes, cartilage cells, tendon cells, adipose cells and the like), and capable of proliferating while keeping the capability. The term "mesenchymal stem cells" as used in the present invention refers to cells same as mesenchymal stromal cells and the two are not particularly differentiated. In addition, the term is simply denoted as mesenchymal cells. Examples of tissue containing mesenchymal stem cells include adipose tissue, umbilical cord, bone marrow, umbilical cord blood, endometrial, placenta, amnion, chorion, decidua, dermis, skeletal muscle, periosteum, dental sac, periodontal ligament, dental pulp, and tooth germ. For example, the term "adipose tissue-derived mesenchymal stem cells" refers to mesenchymal stem cells contained in adipose tissues, and may also be referred to as adipose tissue-derived mesenchymal stromal cells. Of these tissues, in view of efficacy for treatment of liver disease and availability and the like, adipose tissue-derived mesenchymal stem cells, umbilical cord-derived mesenchymal stem cells, bone marrow-derived mesenchymal stem cells, placenta-derived mesenchymal stem cells and dental pulp-derived mesenchymal stem cells are preferable; and adipose tissue-derived mesenchymal stem cells and umbilical cord-derived mesenchymal stem cells are more preferable.

Mesenchymal stem cells in the present invention may be derived from the same species as or different species from that of a subject to be treated (test subject). Examples of the species of mesenchymal stem cells in the present invention include human, horse, cattle, sheep, pig, dog, cat, rabbit, mouse and rat, and preferably the mesenchymal stem cells are cells derived from the same species as that of a subject to be treated (test subject). The mesenchymal stem cells in the present invention may be derived from a subject to be treated (test subject); that is, isogenic (autologous) cells, or may be derived from another subject of the same species; that is, may be allogeneic cells. The mesenchymal stem cells are preferably allogeneic cells.

Mesenchymal stem cells are unlikely to cause rejection also in an allogenic test subject. Therefore, previously prepared donor cells subjected to expansion culture and then cryopreservation can be used as mesenchymal stem cells in the therapeutic agent for diseases of the present invention. Accordingly, compared with a case in which autologous mesenchymal stem cells are prepared for use, mesenchymal stem cells in the present invention are more preferably allogenic in view of easy commercialization and ease of obtaining some stable effectiveness.

The term "mesenchymal stem cells" in the present invention refers to any cell population containing mesenchymal stem cells. Such a cell population comprises at least 20% or more, preferably 30%, 40%, 50%, 60%, 70%, 75%, 80%, 85%, 90%, 93%, 96%, 97%, 98% or 99% of mesenchymal stem cells.

The term "adipose tissue" in the present invention refers to tissue containing adipose cells and mesenchymal stem cells including microvascular cells and the like, which can be obtained through surgical resection or suction of subcutaneous fat of mammals, for example. Adipose tissue can be obtained from subcutaneous fat. Adipose tissue is preferably obtained from animals of the same species as that of a test subject to which adipose tissue-derived mesenchymal stem cells are administered as described later. In view of administration to humans, adipose tissue is more preferably human subcutaneous fat. A donor (individual) from which subcutaneous fat is supplied may be alive or dead, however, adipose tissue to be used in the present invention is preferably tissue collected from a living individual. When adipose tissue is collected from an individual, examples of liposuction include PAL (power-assisted) liposuction, elcornia laser liposuction, and body jet liposuction. In view of maintaining cell status, preferably no ultrasonic wave is used.

The umbilical cord in the present invention is a white tubular tissue connecting between the fetus and the placenta, is composed of umbilical cord veins, umbilical cord arteries, mucous connective tissue (Wharton's Jelly), umbilical cord matrix itself, and the like, and is rich in mesenchymal stem cells. The umbilical cord is preferably obtained from animals of the same species as that of a test subject (a subject to which the agent is administered) for which the therapeutic agent for diseases of the present invention is used. In view of administration of the therapeutic agent for diseases of the present invention to humans, the umbilical cord is more preferably human umbilical cord.

The term "bone marrow" in the present invention refers to spongy tissue filling the bone lumen and is a hematopoietic organ. Bone marrow aspirate is present in the bone marrow, and cells existing therein are referred to as "bone marrow cells". Bone marrow cells include, in addition to erythrocytes, granulocytes, megakaryocytes, lymphocytes, adipose cells and the like, mesenchymal stem cells, hematopoietic stem cells, vascular endothelial precursor cells, and the like. Bone marrow cells can be collected from human ilia, long bones, or other bones, for example.

The term "mesenchymal stem cells derived from each tissue" in the present invention such as adipose tissue-derived mesenchymal stem cells, umbilical cord-derived mesenchymal stem cells, and bone marrow-derived mesenchymal stem cells refer to any cell population containing mesenchymal stem cells derived from each tissue such as adipose tissue-derived mesenchymal stem cells, umbilical cord-derived mesenchymal stem cells, and bone marrow-derived mesenchymal stem cells, respectively. Such a cell population comprises at least 20% or more, preferably 30%, 40%, 50%, 60%, 70%, 75%, 80%, 85%, 90%, 93%, 96%, 97%, 98% or 99% of mesenchymal stem cells derived from each tissue such as adipose tissue-derived mesenchymal stem cells, umbilical cord-derived mesenchymal stem cells, and bone marrow-derived mesenchymal stem cells.

In the present invention, the mesenchymal stem cells may be characterized in that the expression of TFPI is high, in addition, characterized by, for example, growth characteristics (e.g., population doubling capability or doubling time required from passages to senescence), karyotype analysis (e.g., normal karyotype; maternal or neonatal sequence), surface marker expression as determined by flow cytometry (e.g., FACS analysis), immunohistochemistry and/or immunocytochemistry (e.g., epitope detection), gene expression profiling (e.g., gene chip arrays; polymerase chain reaction such as reverse transcription PCR, real time PCR, and conventional PCR)), miRNA expression profiling, protein arrays, secretion of proteins such as cytokines (e.g., analysis of plasma clotting, ELISA, and cytokine arrays) metabolites (metabolome analysis), other methods known in the art, and the like.

(Method for Preparing Mesenchymal Stem Cells)

A method for preparing high-TFPI expression mesenchymal stem cells is not particularly limited. Preparation can be carried out as follows: mesenchymal stem cells can be obtained by separating mesenchymal stem cells from a tissue such as an adipose tissue, umbilical cord or bone marrow in accordance with a method known to a person skilled in the art, culturing the mesenchymal stem cells and separating high-TFPI expression mesenchymal stem cells by e.g., a cell sorter or magnetic beads using an anti-TFPI antibody specifically binding to TFPI. Alternatively, high-TFPI expression mesenchymal stem cells can be obtained by inducing expression of TFPI in the mesenchymal stem cells by culture using a specific medium. In the cell population obtained by the induction, preferably 50% or more of the cells constituting the population is high-TFPI expression cells, more preferably 70% or more thereof is high-TFPI expression cells; further preferably 80% or more thereof is high-TFPI expression cells and particularly preferably 90% or more thereof is high-TFPI expression cells. Most preferably, the cell population is a homogeneous population substantially consisting of high-TFPI expression cells. A method for preparing high-TFPI expression mesenchymal stem cells will be specifically described below.

Mesenchymal stem cells can be prepared by a method well-known by persons skilled in the art. A method for preparing adipose tissue-derived mesenchymal stem cells is described below as an example. Adipose tissue-derived mesenchymal stem cells may be obtained, for example, by the production method disclosed in U.S. Pat. No. 6,777,231, and can be produced, for example, by a method comprising the following steps (i) to (iii):

(i) step of obtaining a cell suspension by enzymatic digestion of adipose tissue;
(ii) step of precipitating cells for re-suspension of cells in an appropriate medium; and
(iii) step of culturing cells on a solid surface and then removing cells not binding to the solid surface.

The adipose tissue to be used in step (i) is preferably washed. The tissue can be washed with a physiologically compatible physiological saline solution (for example, phosphate buffer saline (PBS)) while vigorously stirring, and then, allowed to precipitate. This is for removing undesired substances (also referred to as debris, for example, damaged tissue and blood such as red blood cells) from the tissue. Accordingly, the wash/precipitation will be repeated until the debris is totally removed from the supernatant. Since the remaining cells are present as clumps different in size, it is preferable that the cell clumps obtained are washed and treated with an enzyme (for example, collagenase, dispase or trypsin) that weakens or destroys intercellular binding in order to mutually dissociate clumps while minimizing damage of the cells themselves. The amount of such an enzyme and a treatment time thereof, which vary depending on the use conditions, are known in this technical field. Cell clumps can be dissociated by using other treatment methods using mechanical stirring, ultrasonic energy and thermal energy in place of or in combination with such an enzymatic treatment. However, in order to minimize cell damage, an enzymatic treatment alone is preferably used. If an enzyme is used, in order to minimize harmful effects to cells, the enzyme is desirably inactivated by use of, e.g., a medium after an appropriate period of time.

The cell suspension obtained in the step (i) contains a slurry or suspension of aggregated cells and various undesirable cells, such as red blood cells, smooth muscle cells, endothelial cells and fibroblasts. The aggregated cells and the undesirable cells may be separated and removed; however since removal can be made by adhesion and washing in the step (iii) described later, separation/removal herein may be skipped. Separation and removal of undesirable cells can be achieved by centrifugation for forcibly separating cells into the supernatant and the sediment. The sediment containing undesirable cells is suspended in a physiologically compatible solvent. The cell suspension may be at a risk of containing red blood cells; however, red blood cells can be selectively removed by adhesion to a solid surface (described later). Because of this, a step of lysing red blood cells is not necessary. As a method for selectively lysing red blood cells, a method known in the art, such as lysis with ammonium chloride through incubation in a hypertonic medium or hypotonic medium, can be used. After lysis, a lysate may be separated from desired cells, for example, by filtration, centrifugal sedimentation or density fractionation.

In the step (ii), to increase purity of mesenchymal stem cells in a cell suspension, washing is carried out once or continuously a plurality of times, centrifugation and resuspension in a medium may be carried out. Other than this, cells may be separated based on a cell surface marker profile or cell size and granularity.

The medium to be used for resuspension is not particularly limited as long as the mesenchymal stem cells can be cultured. Such a medium may be prepared by adding a serum in a basal medium and/or adding at least one serum substitute such as albumin, transferrin, a fatty acid, insulin, sodium selenite, cholesterol, collagen precursor, a trace element, 2-mercaptoethanol and 3'-thiol glycerol. If necessary, substances such as lipids, amino acids, proteins, polysaccharides, vitamins, growth factors, small molecule compounds, antibiotic substances, antioxidants, pyruvic acids, buffers and inorganic salts may be added to such medium.

Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, MCDB201 medium and a mixed medium of these.

Examples of the serum include, but are not limited to, human serum, fetal calf serum (FBS), bovine serum, calf serum, goat serum, horse serum, porcine serum, sheep serum, rabbit serum and rat serum. If a serum is used, the serum may be added in a ratio of 5 v/v % to 15 v/v %, preferably 10 v/v % relative to the basal medium.

Examples of the fatty acid include, but are not limited to, linoleic acid, oleic acid, linolenic acid, arachidonic acid, myristic acid, palmitoyl acid, palmitic acid and stearic acid. Examples of the lipid include, but are not limited to, phosphatidylserine, phosphatidyl ethanolamine and phosphatidyl choline. Examples of the amino acid include, but are not limited to, L-alanine, L-arginine, L-aspartic acid, L-asparagine, L-cysteine, L-cystine, L-glutamic acid, L-glutamine and L-glycine. Examples of the protein include, but are not limited to, ecotin, reduced glutathione, fibronectin and β2-microglobulin. Examples of the polysaccharide include, but are not limited to, a glycosaminoglycan such as hyaluronic acid and heparan sulfate. Examples of growth factors include, but are not limited to, platelet-derived growth factor (PDGF), basic fibroblast growth factor (bFGF), transforming growth factor β (TGF-β), hepatocyte growth factor (HGF), epidermal growth factor (EGF), connective tissue growth factor (CTGF) and vascular endothelial growth factor (VEGF). In order to use adipose-derived mesenchymal stem cells obtained in the present invention for cell transplantation, it is preferable to use a xeno-free medium not containing a xenogeneic component(s) such as a serum. As a medium, a commercially available ready-made medium for mesenchymal stem cells (stromal cells) is provided by a manufacturer such as PromoCell GmbH, Lonza, Biological Industries, Veritas, R&D Systems, Corning Inc. and Rohto Pharmaceutical Co., Ltd.

Subsequently, in the step (iii), the cells contained in the cell suspension obtained in the step (ii) are cultured, without separating them, on a solid surface by using an appropriate cell medium as mentioned above at an appropriate cell density and culture conditions. In the present invention, the "solid surface" refers to any material to which the mesenchymal stem cells of the present invention derived from an adipose tissue can bind or adhere. In a particular embodiment, such a material may be a plastic material, the surface of which is treated to promote binding or adhesion of mammalian cells. As a culture vessel having such a solid surface, although the shape thereof is not particularly limited, e.g., a petri dish and a flask, can be preferably used. To remove unbound cells and cell debris, cells are washed after incubation.

In the present invention, cells finally remaining in the state of binding and adhering to the solid surface, can be selected as a cell population of adipose tissue-derived mesenchymal stem cells.

To confirm that the selected cells are the mesenchymal stem cells derived from an adipose tissue according to the present invention, a surface antigen may be analyzed by, e.g., flow cytometry, in accordance with a conventional method. The cells may be examined for an ability to differentiate to various cell lines in accordance with a conventional method.

In the present invention, the mesenchymal stem cells can be prepared as described above and can be defined as the cells having the following characteristics,
(1) adhesive to a plastic material in a culture conditions in a standard medium,
(2) surface antigens CD44, CD73 and CD90 are positive; whereas, surface antigens CD31 and CD45 are negative, and
(3) capable of differentiating into osteocytes, adipocytes and chondrocytes in culture conditions.

The mesenchymal stem cells expressing TFPI protein at a high level can be obtained by selectively separating the cells expressing TFPI protein at a high level from the mesenchymal stem cells obtained in the step (iii) by an immunological method using, e.g., a cell sorter or magnetic beads. The high-TFPI expression mesenchymal stem cells can be efficiently obtained by inducing expression of TFPI in the mesenchymal stem cells by culturing the mesenchymal stem cells in a predetermined medium which can induce expression of TFPI. For example, a method for selectively separating the cells by an immunological method using a cell sorter will be more specifically described, below.

A cell suspension obtained by treating the mesenchymal stem cells prepared above with, e.g., a trypsin/EDTA solution, is centrifuged (room temperature, 400G, 5 minutes) and the supernatant is removed. To the cells obtained, a staining buffer (1% BSA-PBS) is added and the concentration is controlled to be $1 \times 10^6$ cells/500 µL, and after the cell suspension is homogenized with pipetting to obtain a uniform cell concentration, the cell suspension is dispensed to new 1.5 mL micro tubes in a volume of 50 µL per tube. To the cell suspension dispensed, a primary antibody (ADG4903, mouse anti human TFPI, manufactured by Sekisui Diagnostics) is added in a concentration of 5 to 20 µg/mL and suspended. Thereafter, the cell suspension is allowed to react under a light-proof refrigeration condition for 30 minutes to one hour. After washing is carried out three times with a staining buffer (1 mL), the staining buffer is added to adjust a volume of 50 µL. To this, a secondary antibody (A21202, anti-mouse IgG alexar488, manufactured by Thermo Fisher Scientific) is added in a concentration of 1 to 10 μg/mL and suspended. Thereafter, the cell suspension is allowed to react under a light-proof refrigeration condition for 30 minutes to one hour. After washing is carried out three times with a staining buffer (1 mL), 300 μL of PI Buffer (prepared by adding 28.8 μL of a propidium iodide solution (P4864, manufactured by SIGMA) to 14.4 mL of the staining buffer) is added, suspended well, passed through a tube equipped with a cell strainer and can be separated by fluorescence activated cell sorting (FACS).

(Cryopreservation of Mesenchymal Stem Cells)

In the present invention, the mesenchymal stem cells may be those obtained by repeatedly and appropriately cryopreserving and thawing, as long as the cells have an effect for treating diseases. In the present invention, cryopreservation can be carried out by suspending mesenchymal stem cells in a cryopreservation solution known to a person skilled in the art and cooling the cells. The suspension can be carried out by removing cells with a remover such as trypsin, transferring the cells in a cryopreservation container, appropriately treating the cells and adding a cryopreservation solution.

The cryopreservation solution may contain DMSO (dimethyl sulfoxide) as a cryoprotective agent; however, DMSO has not only a cytotoxicity and a property for inducing differentiation of the mesenchymal stem cells. Because of this, it is preferable to reduce the content of DMSO. As a substitute for DMSO, glycerol, propylene glycol or polysaccharidel are mentioned. If DMSO is used, the concentration of DMSO is 5% to 20%, preferably 5% to 10% and more preferably 10%. Other than DMSO, an additive(s) described in WO2007/058308 may be contained. Such a cryopreservation solution, for example, cryopreservation solutions provided by companies such as Bio Verde Corporation, Nippon Genetics Co., Ltd., REPROCELL, ZENOAQ (Nippon Zenyaku Kogyo Co., Ltd.), COSMO BIO, KOHJIN BIO and Thermo Fisher Scientific, may be used.

When the suspended cells are cryopreserved, it is sufficient that the cells are preserved at a temperature between −80° C. and −100° C. (for example, −80° C.). Cryopreservation can be attained by use of a freezer that can reduce the temperature up to the above temperature. To avoid a rapid temperature change, a cooling rate may be appropriately controlled by use of a program freezer; however, the control means is not limited. The cooling rate may be appropriately selected depending on the components of a cryopreservation solution. Selection can be carried out in accordance with instructions of a manufacturer of a cryopreservation solution.

The preservation period, in other words, upper limit of the period, is not particularly limited as long as the cells cryopreserved in the above conditions and thawed have the equivalent properties as those before cryopreserved. As the upper limit, 1 week or more, 2 weeks or more, 3 weeks or more, 4 weeks or more, 2 months or more, 3 months or more, 4 months or more, 5 months or more, 6 months or more or one year or more is mentioned. Since cell damage can be suppressed by preserving the cells at a lower temperature, the cells may be transferred to a gaseous phase above liquid nitrogen (about −150° C. or lower to −180° C. or higher) and preserved there. If the cells are preserved in a gaseous phase above liquid nitrogen, preservation can be made by using a preservation container known to a person skilled in the art. If the cells are preserved for 2 weeks or more, the cells are preferably preserved in a gaseous phase above liquid nitrogen; however, the preservation place is not particularly limited.

The mesenchymal stem cells thawed may be appropriately cultured until a next cryopreservation time. Mesenchymal stem cells are cultured in a medium that can culture the mesenchymal stem cells at a temperature of about 30 to 40° C., preferably about 37° C. under the atmosphere containing $CO_2$; however, the culture conditions are not particularly limited. The concentration of $CO_2$ is about 2 to 5% and preferably about 5%. In the culture, after cells reach an appropriate confluency in a culture vessel (for example, cells occupy 50% to 80% of a culture vessel), the cells may be removed by a remover such as trypsin, seeded in another culture vessel at an appropriate cell density and continuously cultured. When cells are seeded, a typical cell density is, for example, 100 cells/cm$^2$ to 100,000 cells/cm$^2$, 500 cells/cm$^2$ to 50,000 cells/cm$^2$, 1,000 to 10,000 cells/cm$^2$ and 2,000 to 10,000 cells/cm$^2$. In a particular embodiment, the cell density is 2,000 to 10,000 cells/cm$^2$. It is preferable that the period until cells reach an appropriate confluency is controlled to be 3 days to 7 days. During culture, if necessary, the medium may be appropriately exchanged.

Cells cryopreserved can be thawed by a method known to a person skilled in the art, for example, by placing the cells in a thermostat bath or in a hot water bath of 37° C. while standing still or shaking.

The state of the mesenchymal stem cells of the present invention is not limited, for example, recovered cells by removing cultured cells and cells freezed in a cryopreservation solution are acceptable. Use of the cells, which were obtained by proliferation in a same culture lot, segmented into small portions and cryopreserved is preferable, because a stable and same function effect can be obtained and handling of the cells is excellent. Cryopreserved mesenchymal stem cells are thawed just before use and suspended in a cryopreservation solution. The suspended mesenchymal stem cells can be directly blended in a solution such as an infusion or a medium, or the cryopreservation solution is centrifugally removed and the resultant cells may be suspended in a solution such as an infusion or a medium. The "infusion" herein refers to a solution to be used in a therapy for a human. Examples of the infusion include, but are not particularly limited to, physiological saline, Japanese Pharmacopoeia physiological saline, a 5% glucose solution, Japanese Pharmacopoeia glucose injection solution, Ringer's solution, Japanese Pharmacopoeia Ringer's solution, Ringer's lactate solution, Ringer's acetate solution, No. 1 solution (starting solution), No. 2 solution (dehydrated replenisher), No. 3 solution (maintaining solution) and No. 4 solution (postoperative recovery solution).

[Therapeutic Agent for Liver Disease]

The therapeutic agent for liver disease of the present invention contains the mesenchymal stem cells of the present invention mentioned above highly expressing TFPI. The therapeutic agent for liver disease of the present invention can effectively suppress liver fibrosis. To the mesenchymal stem cells contained in the therapeutic agent for liver disease of the present invention, the description in the section "Mesenchymal stem cells" can be applied.

The therapeutic agent for liver disease of the present invention can contain a pharmaceutically acceptable carrier and additives other than the above mesenchymal stem cells in accordance with a customary method and depending on the usage or dosage form thereof as long as the effect of the present invention is not damaged. Examples of such carriers and additives include, but are not limited to, isotonizing agents, thickeners, saccharides, sugar alcohols, antiseptic agents (preservatives), bactericide agents or antimicrobe agents, pH regulators, stabilizers, chelating agents, oil bases, gel bases, surfactants, suspending agents, binders, excipients, lubricants, disintegrants, blowing agents, fluidizers, dispersants, emulsifiers, buffers, solubilizers, antioxidants, sweeteners, acidifiers, colorants, flavoring agents, essences or refreshing agents. As typical components, for example, the following carriers and additives are mentioned.

Examples of the carrier include an aqueous carrier such as water and hydrous ethanol. Examples of the isotonizing agent (inorganic salt) include sodium chloride, potassium chloride, calcium chloride and magnesium chloride. Examples of the polyhydric alcohol include glycerin, propylene glycol and polyethylene glycol. Examples of the thickener include a carboxyvinyl polymer, hydroxyethyl cellulose, hydroxypropyl methylcellulose, methylcellulose, alginic acid, polyvinyl alcohol (completely or partially saponified), polyvinyl pyrrolidone and macro goal. Examples of the sugar include cyclodextrin and glucose. Examples of the sugar alcohol include xylitol, sorbitol and mannitol (these may be any one of d-form, l-form and dl-form). Examples of the antiseptic agent, disinfecting agent or antimicrobial agent include dibutylhydroxytoluene, butylhydroxyanisole, an alkyl diaminoethyl glycine hydrochloride, sodium benzoate, ethanol, benzalkonium chloride, benzethonium chloride, chlorhexidine gluconate, chlorobutanol, sorbic acid, potassium sorbate, trometamol, sodium dehydroacetate, methyl parahydroxybenzoate, ethyl parahydroxybenzoate, propyl parahydroxybenzoate, butyl parahydroxybenzoate, oxyquinoline sulfate, phenethyl alcohol, benzyl alcohol, a biguanide compound (more specifically, e.g., polyhexanide hydrochloride (polyhexamethylene biguanide)) and GLOKILL (brand name, manufactured by Rhodia). Examples of the pH modifier include hydrochloric acid, boric acid, aminoethyl sulfonate, epsilon-aminocaproic acid, citric acid, acetic acid, sodium hydroxide, potassium hydroxide, calcium hydroxide, magnesium hydroxide, sodium hydrogen carbonate, sodium carbonate, borax, triethanolamine, monoethanolamine, diisopropanolamine, sulfuric acid, magnesium sulfate, phosphoric acid, polyphosphoric acid, propionic acid, oxalic acid, gluconic acid, fumaric acid, lactic acid, tartaric acid, malic acid, succinic acid, gluconolactone and ammonium acetate. Examples of the stabilizer include dibutylhydroxytoluene, trometamol, sodium formaldehydesulfoxylate (Longarit), tocopherol, sodium pyrosulfite, monoethanolamine, aluminum monostearate, glycerin monostearate, sodium hydrogen sulfite and sodium sulfite. Examples of the oil base include a vegetable oil such as olive oil, corn oil, soybean oil, sesame oil and cotton seed oil, and a medium-chain fatty acid triglyceride. Examples of the aqueous base include, macro goal 400. Examples of the gel base include a carboxyvinyl polymer and gum substance. Examples of the surfactant include polysorbate 80, hardened castor oil, glycerin fatty acid ester and sorbitan sesquioleate. Examples of the suspending agent include white beeswax, a surfactant, gum Arabic, gum Arabic powder, xanthan gum and soy lecithin. Examples of the binder include hydroxyethyl cellulose, hydroxypropyl cellulose, hydroxypropyl methylcellulose, sodium carboxymethylcellulose, polyvinyl pyrrolidone and polyvinyl alcohol. Examples of the excipient include sucrose, lactose, starch, corn starch, crystalline cellulose and light anhydrous silica acid. Examples of the lubricant include sucrose fatty acid ester, magnesium stearate and talc. Examples of the disintegrant include hydroxypropyl cellulose (low degree of substitution), crospovidone and croscarmellose sodium. Examples of the blowing agent include sodium hydrogen carbonate. Examples of the fluidizer include, sodium aluminometasilicate and light anhydrous silicic acid.

The therapeutic agent for liver disease of the present invention can be provided in various dosage forms such as a solid agent, a semisolid agent and a liquid agent, depending on the purpose. For example, the mesenchymal stem cells of the present invention can be used as a solid agent (e.g., a tablet, a powder, a powdered drug, a granule, a capsule), a semisolid agent [e.g., an ointment (e.g., a hard ointment, a soft ointment), a cream], a liquid agent [e.g., a lotion, an extract, a suspending agent, an emulsion, a syrup, an injection (including an infusion solution, an implant injection, a continuous injection, an injection prepared before use), a dialysis agent, an aerosol agent, a soft capsule, a drink agent], a patch and a poultice. The therapeutic agent for liver disease of the present invention can be used in a dosage form such as a solution in an oily vehicle or an aqueous vehicle, or an emulsion. Further, the therapeutic agent for liver disease of the present invention can be applied to an affected area by spraying. The therapeutic agent for liver disease of the present invention can be used in a dosage form which is designed to forming a gel or sheet after sprayed to an affected area. The therapeutic agent for liver disease of the present invention can be applied in such a way that the cells form into a sheet-like form or a three dimensional structure, and then, are applied to an affected area.

The therapeutic agent for liver disease of the present invention can be used by suspending or diluting the cells with an infusion such as physiological saline, Japanese Pharmacopoeia physiological saline, a 5% glucose solution, Japanese Pharmacopoeia glucose injection solution, Ringer's solution, Japanese Pharmacopoeia Ringer's solution, Ringer's lactate solution, Ringer's acetate solution, Ringer's bicarbonate solution, No. 1 solution (starting solution), No. 2 solution (dehydrated replenisher), No. 3 solution (maintaining solution), and No. 4 solution (postoperative recovery solution), or a cell culture medium such as DMEM; preferably with physiological saline, a 5% glucose solution or No. 1 solution (starting solution); and more preferably with a 5% glucose solution or No. 1 solution (starting solution).

If the therapeutic agent for liver disease of the present invention is a liquid, the pH of the therapeutic agent for liver disease is not particularly limited as long as it is within the pharmacologically (pharmaceutically) or physiologically acceptable range. The range is, for example, 2.5 to 9.0, preferably 3.0 to 8.5 and more preferably 3.5 to 8.0.

When the therapeutic agent for liver disease of the present invention is a liquid, the osmotic pressure of the therapeutic agent for liver disease is not particularly limited as long as it is within the acceptable range for a living body. The osmotic pressure ratio of the composition of the present invention, for example, preferably is within the range 0.7 to 5.0, more preferably 0.8 to 3.0 and further preferably 0.9 to 1.4. The osmotic pressure is controlled by use of, e.g., an inorganic salt, a polyhydric alcohol, a sugar alcohol and/or sugar in accordance with a method known to the art. The osmotic pressure ratio is defined as the ratio of the osmotic pressure of a sample relative to the osmotic pressure of a 0.9 w/v % sodium chloride solution (i.e., 286 mOsm) and measured in accordance with the osmometry (freezing point method) described in the 15th amended Japanese Pharmacopoeia. Note that, the standard solution (0.9 w/v % sodium chloride solution) for measuring an osmotic pressure ratio is prepared, after sodium chloride (Japanese Pharmacopoeia standard reagent) is dried at 500 to 650° C. for 40 to 50 minutes and cooled in a desiccator (silica gel), by accurately weighing 0.900 g of the sodium chloride obtained, dissolving it in purified water and accurately controlling the volume of the solution to be 100 mL; or a commercially available standard solution for measuring an osmotic pressure ratio (0.9 w/v % sodium chloride solution) is used.

Examples of the administration route of the therapeutic agent for liver disease of the present invention to a subject include oral administration, subcutaneous administration, intramuscular administration, intravenous administration, intra-arterial administration, intraspinal administration, intraperitoneal administration, sublingual administration, transrectal administration, transvaginal administration, intraoculaer administration, transnasal administration, inhalation, transdermal administration, implant and direct administration by spraying an agent and attaching a sheet to the surface of a liver. In view of effectiveness of the therapeutic agent for liver disease of the present invention, implant, hepatic arterial administration, intravenous administration and direct administration by spraying an agent and attaching a sheet to the surface of a liver, are preferable. In view of reduction of burden to a subject, intravenous administration is more preferable.

The dose of the therapeutic agent for liver disease of the present invention can vary depending on, e.g., the state (e.g., body weight, age, symptom, physical conditions) of the patient and the dosage form of a therapeutic agent for liver disease of the present invention. In order to produce a sufficient therapeutic effect of the therapeutic agent for liver disease, it tends to be preferable that the dose is high. In contrast, to suppress a side effect, it tends to be preferable that the dose is low. Usually, in the case of administration to an adult, the dose in terms of a number of cells is $1 \times 10^3$ to $1 \times 10^{12}$ cells/time, preferably $1 \times 10^4$ to $1 \times 10^{11}$ cells/time, more preferably $1 \times 10^5$ to $1 \times 10^{10}$ cells/time, and further preferably $5 \times 10^6$ to $1 \times 10^9$ cells/time. The dose per body weight of a patient is $1 \times 10$ to $5 \times 10^{10}$ cells/kg, preferably $1 \times 10^2$ to $5 \times 10^9$ cells/kg, more preferably $1 \times 10^3$ to $5 \times 10^8$ cells/kg and further preferably $1 \times 10^4$ to $5 \times 10^7$ cells/kg. Note that, this dose, which is defined as the amount per administration, may be administered a plurality of times or this dose is divided into a plurality of portions and administered.

The therapeutic agent for liver disease of the present invention may be administered in combination with one or two or more medicinal agents. As the medicinal agent, any medicinal agent(s) may be used. Examples of the medicinal agent include a therapeutic agent for liver, for example, a therapeutic agent for hepatitis B (e.g., lamibudine, adefovir, entecavir, tenofovir), interferon preparation (e.g., interferon α, interferon α-2b, interferon β, peginterferon α-2a, peginterferon α-2b), a therapeutic agent for hepatitis C (e.g., ribavirin, Telaprevir, Simeprevir, Vaniprevir, Daclatasvir, Asunaprevir, Sofosbuvir), corticosteroid (e.g., prednisolone, methylprednisolone sodium succinate), an anticoagulant (e.g., dried concentrated human antithrombin III, gabexate mesilate, thrombomodulin α), a detoxicating agent (calcium disodium edetate hydrate, glutathione, dimethycaprole, sodium thiosulfate hydrate, sugammadex sodium), human serum albumin, liver extract, ursodeoxycholic acid, glycyrrhizinic acid, Azathioprine, bezafibrate, amino acids (e.g., glycine, L-cysteine, L-isoleucine, L-leucine, L-valine, L-threonine, L-serine, L-alanine, L-methionine, L-phenylalanine, L-tryptophan, L-ricin, L-histidine, L-arginine and salts of these), vitamin (e.g., tocopherol, flavin adenine dinucleotide, thiamine disulfide phosphate, pyridoxine, cyanocobalamin and salts of these), and antibiotic substances (e.g., sodium sulbactam, sodium cefoperazone, meropenem hydrate, vancomycin hydrochloride).

The mesenchymal stem cells of the present invention can be used for various liver diseases and liver disorders. Examples of the diseases include liver diseases such as autoimmune hepatitis, fulminant hepatitis, chronic hepatitis, viral hepatitis, alcoholic hepatitis, nonalcoholic fatty liver disease (NAFLD), non-alcoholic steatohepatitis (NASH), non-alcoholic fatty liver (NAFL), liver fibrosis, liver cirrhosis, liver cancer, fatty liver, drug-induced allergic liver disease, hemochromatosis, hemosiderosis, Wilson's disease, primary biliary cirrhosis (PBC), primary sclerosing cholangitis (PSC), biliary atresia, liver abscess, chronic active hepatitis and chronic persistent hepatitis. Of them, the mesenchymal stem cells of the present invention are preferably used for diseases associated with liver tissue fibrosis such as liver fibrosis and liver cirrhosis since the mesenchymal stem cells have a fibrosis suppression effect.

<Method for Treating Liver Disease>

According to another aspect of the present invention, the present invention includes a method for treating liver disease, characterized by using mesenchymal stem cells highly expressing a Tissue Factor Pathway Inhibitor (TFPI). More specifically, according to the present invention, it is possible to treat and ameliorate liver disease, particularly liver disease associated with fibrosis, by administering the mesenchymal stem cells highly expressing a Tissue Factor Pathway Inhibitor (TFPI) to a patient with liver disease. Note that, to the mesenchymal stem cells to be used in the treatment method of the present invention, the descriptions of the section [Mesenchymal stem cells] above and the section [Therapeutic agent for liver disease] can be applied.

EXAMPLES

Now, the present invention will be more specifically described by way of Examples and Experimental Examples; however, the present invention is not limited by these Examples.

1. Examination of Effect of rTFPI for Suppressing Fibrosis of Human Hepatic Stellate Cells

[Culture of Human Hepatic Stellate Cells]

A cryopreserved suspension of human hepatic stellate cells ((HHSteC), product number: 5300, manufactured by ScienCell Research Laboratories) was thawed by soaking the suspension in a constant-temperature bath of 37° C. To the HHSteC suspension solution thawed, Stellate Cell Medium (product number: 5301, manufactured by ScienCell Research Laboratories) was added so as to obtain a total volume of 2 mL. An aliquot of 15 µL was taken from the HHSteC suspension solution and blended with the equivalent amount of a Trypan Blue solution (0.4%), and then, the numbers of living cells and dead cells were determined. The cell suspension solution required for seeding was taken and transferred to a new 15 mL-centrifuge tube (manufactured by Sumitomo Bakelite Co., Ltd.). To the HHSteC suspension thus taken, Stellate Cell Medium was added so as to obtain a total volume of 30 mL. The resultant suspension was delivered to three POLY-L-Lysine coated 100 mm-dishes (hereinafter referred to as "100 mm-dish", product number: 4020-040, manufactured by IWAKI) in a volume of 10 mL per dish. The 100 mm-dishes having the cells seeded therein were placed in a $CO_2$ incubator (37° C., 5% $CO_2$). One day later, the medium was exchanged with a fresh Stellate Cell Medium and culture was continued. Day 4 after HHSteC were seeded, the medium was removed from the 100 mm-dishes and inside of the dishes was washed with PBS (10 mL). After PBS was removed, 2 mL of StemPro Accutase Cell Dissociation Reagent (A11105-01, Lot. 1750154 manufactured by Thermo Fisher Scientific) was added to each of the 100 mm-dishes. Incubation was carried out in a $CO_2$ incubator for 5 minutes. After the HHSteC suspension solution was transferred to a 50 mL centrifuge tube, Stellate Cell Medium (10 mL) was added to each of the 100 mm-dishes and the remaining HHSteC were collected in the same 50 mL centrifuge tube, which was spun at room temperature and 300×g for 5 minutes by a centrifuge (5702, manufactured by Eppendorf). The supernatant was removed, HHSteC were resuspended in Stellate Cell Medium (10 mL). An aliquot of 15 µL was taken and blended with the equivalent amount of a Trypan Blue solution (0.4%), and then, the numbers of living cells and dead cells were determined. After the volume of the cell suspension solution required for seeding was calculated, the cell suspension was diluted with Stellate Cell Medium so as to obtain a concentration of $7.6 \times 10^4$ cells/mL to prepare a HHSteC suspension solution. The HHSteC were seeded in a 12-well poly-L-lysine coated microplate (hereinafter referred to as "12-well plate", product number: 4815-040, manufactured by IWAKI) in a rate of 1 mL ($7.6 \times 10^4$ cells) per well. The plate was placed in a $CO_2$ incubator (37° C., 5% $CO_2$) and culture was initiated.

[Suppression of Expression of Fibrosis-Related Gene by rTFPI]

One day after initiation of culture, the 12-well plate having HHSteC seeded therein was taken out from the $CO_2$ incubator. The medium of the well corresponding to Group No. 1 was removed, and 1 mL of Stellate Cell Medium (control group) was added. The medium of the well corresponding to Group No. 2 was removed, 1 ng/mL Recombinant TFPI (2974-PI-010, manufactured by R&D Systems) and Stellate Cell Medium were added (TFPI (1 ng/mL) addition group). The medium of the well corresponding to Group No. 3 was removed, 1,000 ng/mL Recombinant TFPI and Stellate Cell Medium were added (TFPI (1,000 ng/mL) addition group). The well plate was placed in a $CO_2$ incubator and culture was carried out for a day. Thereafter, total RNA of HHSteC was recovered and mRNA expression levels of fibrosis related factors, ACTA2 and COL1A1, were determined by quantitative PCR. The primers used herein are described in the following table. The results are shown in FIG. 1 (ACTA2) and FIG. 2 (COL1A1).

TABLE 1

| Name of gene | Gene symbol | NCBI Reference Sequence | Primer sequence Upper stage: Forward primer Lower stage: Reverse primer |
|---|---|---|---|
| collagen, type I, alpha 1 | COL1A1 | NM_000088.3 | AGATCGAGAACATCCGGAG (SEQ ID No. 1) AGTACTCTCCACTCTTCCAG (SEQ ID No.2) |
| actin, alpha2, smooth muscle, aorta | ACTA2 | NM_001141945.2 | CCTTCATCGGGATGGAGTC (SEQ ID No. 3) CCTTCCTGATGTCAATATCACAC (SEQ ID No. 4) |

As shown in FIGS. 1 and 2, expression of mRNA of each of ACTA2 and COL1A1 in HHSteC was suppressed by treatment with rTFPI.

2. Comparison in TFPI Expression Level of Various Cell Strains

Human adipose-derived mesenchymal stem cells (L-ADSC, manufactured by Lonza), human dermal fibroblasts (hDFa, adult, manufactured by Thermo Fisher Scientific), human aortic smooth muscle cells (hASMS, manufactured by Thermo Fisher Scientific) and Hela cells (Hela) were seeded in 6-well plates (#3335, Corning) in a rate of 5,000 cells/cm² and culture was carried out in mediums such as the serum-free medium for mesenchymal stem cells (Rohto Pharmaceutical Co., Ltd.), Cascade Biologics Medium106+LSGS (#M-106-500, Thermo Fisher Scientific), 10% FBS DMEM medium (#D5796, Sigma), and Smooth muscle cell growth medium (#C-22062, Promocell) suitable for individual types of cells, for 3 days. Then, total RNA was recovered and expression of mRNA of TFPI was examined by quantitative PCR. The primers used herein were shown in the following table (custom primers for real time PCR (manufactured by Eurofins Genomics K.K.)). The results are shown in FIG. 3.

TABLE 2

| Name of gene | Gene symbol | NCBI Reference Sequence | Primer sequence Upper stage: Forward primer Lower stage: Reverse primer |
|---|---|---|---|
| tissue factor pathway inhibitor | TFPI | NM_006287.4 | CTGCTGCTTAATCTTGCCC (SEQ ID No. 5) TGGCAACTCCGTATCTGTG (SEQ ID No. 6) |

As shown in FIG. 3, in mesenchymal stem cells cultured in the medium of Rohto Pharmaceutical Co., Ltd., compared to other cells (human dermal fibroblasts (hDFa), human aortic smooth muscle cells (hASMS) and Hela cells), it was found that expression of mRNA of TFPI is high. More specifically, expression of mRNA of TFPI of the mesenchymal stem cells cultured in the medium of Rohto Pharmaceutical Co., Ltd., is 1.34 times as high as that in hDFa, 1.65 times as high as that in hASMS and 2.14 times as high as that in Hela cells.

3. Enhancement of TFPI Expression in Adipose-Derived Mesenchymal Stem Cells

[Preparation of Adipose-Derived Mesenchymal Stem Cells]

After consent was obtained from a human donor, a subcutaneous adipose tissue was obtained by liposuction and washed with physiological saline. To destroy extracellular matrix and isolate cells, collagenase (Roche Diagnostics K.K.) (physiological saline was used as a solvent) was added to the tissue. The mixture was shaken at 37° C. for 90 minutes and dispersed. Subsequently, the suspension solution was centrifuged at 800 g for 5 minutes to obtain a sediment of stromal vascular fractions. To the sediment of cells, the serum-free medium for mesenchymal stem cells (Rohto Pharmaceutical Co., Ltd.) was added and the cell suspension was centrifuged at 400 g for 5 minutes. After the supernatant was removed, the sediment was resuspended in the serum-free medium for mesenchymal stem cells (Rohto Pharmaceutical Co., Ltd.) and the cells were seeded in a flask. The cells were cultured at 37° C. for a few days in 5% $CO_2$. A few days later, a culture was washed with PBS to remove, e.g., blood cells and residual adipose tissue, contained in the culture solution to obtain mesenchymal stem cells attached to a plastic container.

[Analysis of Cell Surface Marker (Flow Cytometry)]

Various surface markers present on adipose tissue-derived mesenchymal stem cells were evaluated by flow cytometry. Adipose tissue-derived mesenchymal stem cells were resuspended in a FACS staining buffer. The antibodies used for FACS analysis were mouse anti-human antibodies CD45, CD73 and CD90 labeled with FITC (fluorescent isocyanine) or PE (phycoerythrin), and the corresponding mouse IgG1 isotype control antibodies. The cells were stained at room temperature for 30 minutes, washed and then analyzed by use of BDFADSCantoII (BD Biosciences, San Jose, Calif.). The data were analyzed by BD FACSDiva SoftwCre (BD Biosciences). As a result, the adipose tissue-derived mesenchymal stem cells (hereinafter referred to as "ADSC") were CD45-negative and CD73- and CD90-positive.

[Cryopreservation of Adipose Tissue-Derived Mesenchymal Stem Cells]

Obtained ADSC were removed by trypsin, transferred to a centrifuge tube and centrifuged at 400×g for 5 minutes to obtain the cells as a sediment. After the supernatant was removed, a cell cryopreservation solution (STEM-CELL-BANKER (ZENOAQ Co., Ltd.)) was added in an appropriate amount to suspend the cells. The cell suspension solution was dispensed in cryotubes and preserved in the freezer at −80° C., transferred to a gaseous phase above liquid nitrogen and continuously preserved.

[Enhancement of TFPI Expression in Adipose-Derived Mesenchymal Stem Cells]

ADSC were cultured from P2 to P4 separately in the serum-free medium for mesenchymal stem cells (Rohto Pharmaceutical Co., Ltd.), ProAD (Procal; manufactured by Rohto Pharmaceutical Co., Ltd.), a serum-free medium (manufactured by Lonza) and a 10% FBS medium, and frozen stocks were prepared. P4 cells of individual stocks were thawed and seeded in 6-well plates, respectively in a rate of 5,000 cells/cm² and cultured in respective 4 types of mediums for 3 days. Then, total RNAs, proteins and culture supernatants were recovered. The expressions of mRNA and protein of TFPI were detected by using quantitative PCR (FIG. 4) and western blot (FIG. 5), respectively. The concentrations of TFPI in the culture supernatants were measured by Human TFPI Quantikine ELISA Kit (#DTFP10, R & D systems) (FIG. 6).

In any one of the serum-free mediums, compared to the 10% FBS medium, it was found that mRNA expression level of TFPI (FIG. 4) and the protein expression level of TFPI (FIG. 5) are high. As shown in FIG. 6, in any one of the serum-free mediums, compared to the 10% FBS medium, it was found that the amount of TFPI secreted in the culture supernatant is significantly high. More specifically, mRNA expression level of TFPI in mesenchymal stem cells cultured in the serum-free medium for mesenchymal stem cells manufactured by Rohto Pharmaceutical Co., Ltd., was 1.16 times as high as those cultured in the Procal medium, 2.64 times as high as those cultured in the Lonza medium; and 6.92 times as high as those cultured in the 10% FBS medium. The amounts of TFPI secreted in the culture supernatants were as follows: the amount (pg/mL) of TFPI secreted in the culture supernatant in the serum-free medium for mesenchymal stem cells manufactured by Rohto Pharmaceutical Co., Ltd., was 2.54 times as high as those in the Procal medium; 5.43 times as high as those in the Lonza medium; and 5.83 times as high as those in the 10% FBS medium.

4. Enhancement of Antifibrotic Activity in Adipose-Derived Mesenchymal Stem Cells Similarly to Section 3 above, ADSC were cultured from P2 to P4 separately in the serum-free medium for mesenchymal stem cells (Rohto Pharmaceutical Co., Ltd.), Lonza serum free medium (manufactured by Lonza) and the 10% FBS medium, and then, frozen stocks were prepared.

ADSC cryopreserved were soaked in a constant-temperature bath at 37° C. and cell suspension solutions were thawed, partly transferred to 15 mL centrifuge tubes, diluted separately with the serum-free medium for mesenchymal stem cells (Rohto Pharmaceutical Co., Ltd.), the serum-free medium (manufactured by Lonza) and the 10% FBS medium, up to 10 mL, and centrifuged at room temperature and 400×g for 5 minutes by a centrifuge (5702, manufactured by Eppendorf). After centrifugation, the supernatant was removed. Each medium (6 mL) was added. An aliquot of 15 µL was taken from the cell suspension and blended with the equivalent amount of a Trypan Blue solution (0.4%). The numbers of living cells and dead cells were determined. The cells required for seeding were transferred to new 15 mL centrifuge tubes and individual mediums were added. The concentration of the living cells was controlled to be $1.52 \times 10^4$ cells/mL. On individual wells of a 12-well plate, a transwell insert (#3460, Corning) was provided. In the lower compartment thereof, each medium (1 mL) was added; whereas, in the transwell insert, ADSC (0.5 mL) prepared so as to contain living cells in a concentration of $1.52 \times 10^4$ cells/mL were separately added. In this manner, the cells were seeded. The 12-well plates were placed in a $CO_2$ incubator (37° C., 5% $CO_2$) and culture was initiated. One day after initiation of culture, the plates having the cells seeded were taken out from the $CO_2$ incubator (37° C., 5% $CO_2$) and the medium in the lower compartment was discarded and the compartment was washed with PBS (1 mL) and PBS was removed. Stellate Cell medium (1 mL) was added. The medium in each transwell insert was discarded and the transwell insert was washed twice with PBS (0.5 mL) and PBS was removed. Stellate Cell Medium (0.5 mL) was added.

Similarly to Section 1 above, 12-well plates on which HHSteC were seeded and cultured for one day were taken out from a $CO_2$ incubator. Then medium was removed from each well and Stellate Cell medium (1 mL) was added. On the well corresponding to Group No. 1 (Control group), a vacant transwell insert was provided and Stellate Cell medium (0.5 mL) was added. On the wells corresponding to Group Nos. 2 to 4, transwell inserts, which were prepared by seeding ADSC, which were cultured in the serum-free medium for mesenchymal stem cells (Rohto Pharmaceutical Co., Ltd., Rohto group), serum-free medium (manufactured by Lonza, Lonza group) and 10% FBS medium (10% FBS group), were provided. The plates having the transwell insert provided were placed in a $CO_2$ incubator (37° C., 5% $CO_2$) and co-culture of HHSteC and ADSC was initiated. One day after initiation of the co-culture, total RNA of HHSteC was recovered and the expression level of mRNA of fibrosis related factors, ACTA2 and COL1A1, was determined by quantitative PCR. The results are shown in FIG. 7 (ACTA2) and FIG. 8 (COL1A1).

The mRNA expressions of ACTA2 and COL1A1 in HHSteC were significantly suppressed by co-culture with ADSC. Also, it was confirmed that the suppression effect of ADSC cultured in the serum-free medium for mesenchymal stem cells (Rohto Pharmaceutical Co., Ltd.) is significantly high compared to that of ADSC cultured in the serum medium.

INDUSTRIAL APPLICABILITY

Owing to the present invention, novel mesenchymal stem cells and a therapeutic agent for liver disease containing the cells are provided.

The invention claimed is:

1. A method for treating liver disease associated with fibrosis of liver tissue, comprising administering adipose tissue derived mesenchymal stem cells to a subject having the liver disease associated with fibrosis of liver tissue, wherein an expression of mRNA or protein of Tissue Factor Pathway Inhibitor (TFPI) in the adipose tissue derived mesenchymal stem cells is at least 1.5 times higher compared to mesenchymal stem cells obtained under a culture in a 10% FBS-containing DMEM medium.

2. The method according to claim 1, wherein the adipose tissue derived mesenchymal stem cells are allogeneic cells that are derived from another subject of the same species.

* * * * *